United States Patent
Miyawaki

(10) Patent No.: US 11,762,156 B2
(45) Date of Patent: Sep. 19, 2023

(54) OPTICAL MODULE FOR ENDOSCOPE, ENDOSCOPE, AND MANUFACTURING METHOD OF OPTICAL MODULE FOR ENDOSCOPE

(71) Applicant: OLYMPUS CORPORATION, Tokyo (JP)

(72) Inventor: Takahide Miyawaki, Nagano (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 17/079,954

(22) Filed: Oct. 26, 2020

(65) Prior Publication Data

US 2021/0096309 A1 Apr. 1, 2021

Related U.S. Application Data

(63) Continuation of application No. PCT/JP2019/017435, filed on Apr. 24, 2019.

(30) Foreign Application Priority Data

Apr. 26, 2018 (WO) .................. PCT/JP2018/017099

(51) Int. Cl.
*G02B 6/42* (2006.01)
*A61B 1/00* (2006.01)
(Continued)

(52) U.S. Cl.
CPC .......... *G02B 6/4239* (2013.01); *A61B 1/0011* (2013.01); *A61B 1/00126* (2013.01);
(Continued)

(58) Field of Classification Search
CPC .. G02B 6/423; G02B 6/4239; G02B 23/2423; G02B 23/24; G02B 23/26; G02B 23/243;
(Continued)

(56) References Cited

U.S. PATENT DOCUMENTS

2014/0097459 A1   4/2014 Motohara

FOREIGN PATENT DOCUMENTS

CN         1548938 A    11/2004
EP         2735899 A1    5/2014
(Continued)

OTHER PUBLICATIONS

International Search Report dated Jul. 16, 2019 issued in PCT/JP2019/017435, 4 pages.

*Primary Examiner* — Thomas A Hollweg
*Assistant Examiner* — Mary A El-Shammaa
(74) *Attorney, Agent, or Firm* — Scully, Scott, Murphy & Presser, P.C.

(57) ABSTRACT

An optical module for endoscope includes an optical fiber, a light emitting element, a ferrule including a front surface and a back surface, and including a first through-hole into which the optical fiber is inserted, a glass substrate including a first principal surface at which the light emitting element is mounted and a second principal surface, a sleeve including a third principal surface bonded to the second principal surface of the glass substrate, and a fourth principal surface, and including a second through-hole into which the ferrule is inserted, and a stopper including a contact surface in surface contact with the back surface of the ferrule, fixed to the sleeve by using an adhesive, and further including an inner side surface in contact with a side surface of the sleeve.

20 Claims, 12 Drawing Sheets

(51) Int. Cl.
 *G02B 23/24* (2006.01)
 *G02B 23/26* (2006.01)
(52) U.S. Cl.
 CPC .......... *A61B 1/00165* (2013.01); *G02B 6/423* (2013.01); *G02B 23/2423* (2013.01); *G02B 23/26* (2013.01); *G02B 23/2484* (2013.01)
(58) Field of Classification Search
 CPC ............ G02B 23/2407; G02B 23/2415; G02B 23/2461; G02B 23/2469; G02B 23/2484; A61B 1/0011; A61B 1/00165; A61B 1/00126
 See application file for complete search history.

(56) References Cited

FOREIGN PATENT DOCUMENTS

| | | | | |
|---|---|---|---|---|
| JP | 2012-242662 | A | 12/2012 | |
| JP | 2013-025092 | A | 2/2013 | |
| KR | 10-2001-0009499 | A | 2/2001 | |
| WO | 2013/011983 | A1 | 1/2013 | |
| WO | 2017/203785 | A1 | 11/2017 | |
| WO | WO-2018037551 | A1 * | 3/2018 | ............... A61B 1/00 |
| WO | WO-2018051679 | A1 * | 3/2018 | ......... A61B 1/00009 |
| WO | WO-2018051680 | A1 * | 3/2018 | ......... A61B 1/00009 |
| WO | WO-2018055933 | A1 * | 3/2018 | ............... A61B 1/00 |
| WO | WO-2018159292 | A1 * | 9/2018 | ............... A61B 1/00 |
| WO | WO-2018180249 | A1 * | 10/2018 | ......... A61B 1/00006 |

\* cited by examiner

OPTICAL MODULE FOR ENDOSCOPE, ENDOSCOPE, AND MANUFACTURING METHOD OF OPTICAL MODULE FOR ENDOSCOPE

CROSS REFERENCE TO RELATED APPLICATION

This application is a continuation application of PCT/JP2019/017435 filed on Apr. 24, 2019 and claims benefit of International Application No. PCT/JP2018/017099 filed on Apr. 26, 2018, the entire contents of which are incorporated herein by this reference.

BACKGROUND OF THE INVENTION

1. Field of the Invention

The present invention relates to an optical module for endoscope including an optical device and an optical fiber, an endoscope including an optical module for endoscope including an optical device and an optical fiber, and a manufacturing method of an optical module for endoscope including an optical device and an optical fiber.

2. Description of the Related Art

An endoscope includes an image pickup device provided at a distal end portion of an elongated insertion section of the endoscope. In recent years, a high resolution image pickup device has been studied for the purpose of displaying high quality images. Using a high resolution image pickup device increases the amount of image signals transmitted from the image pickup device to a signal processing device (processor). Hence, in electrical signal transmission by using metal lines, to transmit a necessary amount of signals, the line diameter of a metal line is increased or a plurality of metal lines are used, and as a result, the insertion section may be widened.

To make the insertion section thinner to achieve minimally invasive operation, it is desirable to transmit optical signals instead of electrical signals through a thin optical fiber. Optical signal transmission employs an E/O optical module (electrical-to-optical converter), which converts an electrical signal into an optical signal, and an O/E optical module (optical-to-electrical converter), which converts an optical signal into an electrical signal.

Japanese Patent Application Laid-Open Publication No. 2013-025092 discloses an optical module including an optical device, a substrate at which the optical device is installed, and a holding section (ferrule) having a through-hole accommodating an inserted optical fiber for transmitting optical signals inputted to or outputted from the optical device.

Japanese Patent Application Laid-Open Publication No. 2012-242662 discloses a socket that can prevent a ferrule holding an optical fiber in a fixed manner from coming out of the socket. A ferrule fixing member presses a back surface of the ferrule fitted into a fitting hole of a circuit board.

Korean Patent Publication No. 10-2001-0009499 discloses a ferrule holder 67 in contact with a back surface of a ferrule 65 and a fourth principal surface of a sleeve 61. The back surface of the ferrule 65 and the fourth principal surface of the sleeve 61 do not lie in the same plane; in other words, one of the two surfaces of the ferrule holder 67 is in contact with the back surface of the ferrule 65 while the other surface is in contact with the fourth principal surface of the sleeve 61.

SUMMARY OF THE INVENTION

An optical module for endoscope of an embodiment includes at least one optical fiber for transmitting an optical signal, at least one optical device for outputting or receiving the optical signal, a ferrule including a front surface and a back surface on an opposite side of the front surface and including a first through-hole, the optical fiber being inserted into the first through-hole, a glass substrate including a first principal surface and a second principal surface on an opposite side of the first principal surface, the optical device being mounted on the first principal surface, a sleeve including a third principal surface and a fourth principal surface on an opposite side of the third principal surface and including a second through-hole, the ferrule being inserted into the second through-hole, the third principal surface being bonded to the second principal surface of the glass substrate, and a stopper including a contact surface in surface contact with the back surface of the ferrule, and an inner side surface in contact with a side surface of the sleeve, and fixed to the sleeve by using an adhesive.

An endoscope of an embodiment includes an optical module for endoscope having at least one optical fiber for transmitting an optical signal, at least one optical device for outputting or receiving the optical signal, a ferrule including a front surface and a back surface on an opposite side of the front surface and including a first through-hole, the optical fiber being inserted into the first through-hole, a glass substrate including a first principal surface and a second principal surface on an opposite side of the first principal surface, the optical device being mounted on the first principal surface, a sleeve including a third principal surface and a fourth principal surface on an opposite side of the third principal surface and including a second through-hole, the ferrule being inserted into the second through-hole, the third principal surface being bonded to the second principal surface of the glass substrate, and a stopper including a contact surface in surface contact with the back surface of the ferrule, and an inner side surface in contact with a side surface of the sleeve, and fixed to the sleeve by using an adhesive.

In a manufacturing method of an optical module for endoscope of an embodiment, the optical module for endoscope includes an optical fiber for transmitting an optical signal, an optical device for outputting or receiving the optical signal, a ferrule including a front surface and a back surface on an opposite side of the front surface and including a first through-hole, a glass substrate including a first principal surface and a second principal surface on an opposite side of the first principal surface, the optical device being mounted on the first principal surface, a sleeve including a third principal surface and a fourth principal surface on an opposite side of the third principal surface and including a second through-hole, and a stopper including a contact surface in surface contact with the back surface of the ferrule. The manufacturing method of the optical module for endoscope includes producing the sleeve including the third principal surface bonded to the second principal surface of the glass substrate, producing the ferrule including the first through-hole, the optical fiber being inserted into the first through-hole, inserting the ferrule into the second through-hole of the sleeve, and pressing the contact surface of the stopper against the back surface of the ferrule while a side surface of the sleeve is maintained in contact with an inner side surface of the stopper and fixing the stopper to the sleeve in a state in which the contact surface is maintained in contact with the back surface.

DETAILED DESCRIPTION OF THE PREFERRED EMBODIMENTS

First Embodiment

Figure 1:
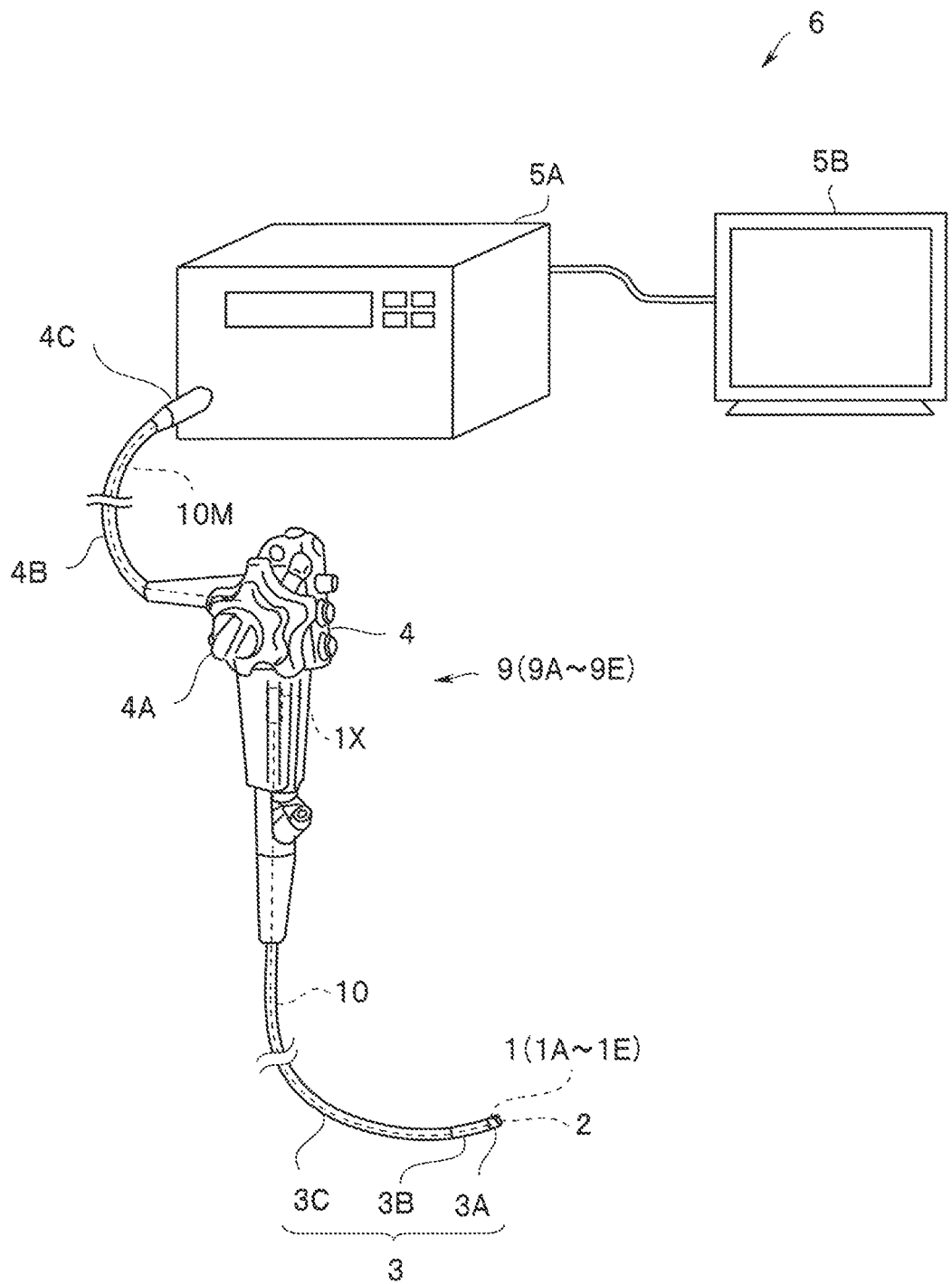
FIG. 1 is a perspective view of an endoscope system including an endoscope having an optical module for endoscope of a first embodiment.

An endoscope 9 of the present embodiment illustrated in FIG. 1 constitutes, together with a processor 5A and a monitor 5B, an endoscope system 6. An optical module for endoscope 1 (hereinafter referred to as "optical module 1") of an embodiment is provided in the endoscope 9.

The endoscope 9 includes an insertion section 3, a grasping section 4 disposed at a proximal end portion of the insertion section 3, a universal cord 4B extending from the grasping section 4, and a connector 4C disposed at a proximal end portion of the universal cord 4B. The insertion section 3 includes a distal end portion 3A, a bendable bending portion 3B extending from the distal end portion 3A and used for changing the direction of the distal end portion 3A, and a flexible portion 3C extending from the bending portion 3B. The optical module 1 and an image pickup device 2 are disposed at the distal end portion 3A. A rotatable angle knob 4A, which is an operation section used by an operator to control the bending portion 3B, is disposed at the grasping section 4.

The connector 4C connects the universal cord 4B to the processor 5A. The processor 5A controls the entire endoscope system 6, and also processes image pickup signals and accordingly output image signals. The monitor 5B displays the image signals outputted by the processor 5A as endoscope images. While the endoscope 9 is a flexible endoscope, the endoscope 9 may be a rigid endoscope. The endoscope 9 can be used for medical or industrial purposes.

The image pickup device 2 and the optical module 1 are disposed at the distal end portion 3A of the endoscope 9. The optical module 1 is an E/O optical module for converting an electrical signal outputted by the image pickup device 2 into an optical signal. The image pickup device 2 is, for example, a complementary metal-oxide semiconductor (CMOS) image sensor or a charge-coupled device (CCD).

The optical signal is transmitted through an optical fiber 10 inserted in the insertion section 3, reconverted into an electrical signal by an O/E optical module 1X disposed at the grasping section 4, and further transmitted through a metal line 10M. This means that in the insertion section 3 of a small diameter an image pickup signal is transmitted through the optical fiber 10; in the universal cord 4B, which is less limited with respect to the outer diameter because the universal cord 4B is not inserted into a human body, an image pickup signal is transmitted through a signal cable 10M that is a metal line thicker than the optical fiber 10.

When an O/E optical module is provided at the connector 4C or the processor 5A, the optical fiber 10 is also inserted in the universal cord 4B.

The optical module 1X is disposed at the grasping section 4 having a relatively wide arrangement space, but the optical module 1X may have the same structure as the structure of the optical module 1. Alternatively, the optical module 1 may be disposed at the grasping section 4 to convert a control signal for the image pickup device 2 into an optical signal; the optical module 1X may be disposed at the distal end portion 3A to convert the optical signal to an electrical signal.

The optical module 1 is small in size and capable of highly reliable performance as will be described later. Thus, the endoscope 9 can achieve minimally invasive and highly reliable operation.

<Optical Module Structure>

Figure 2:
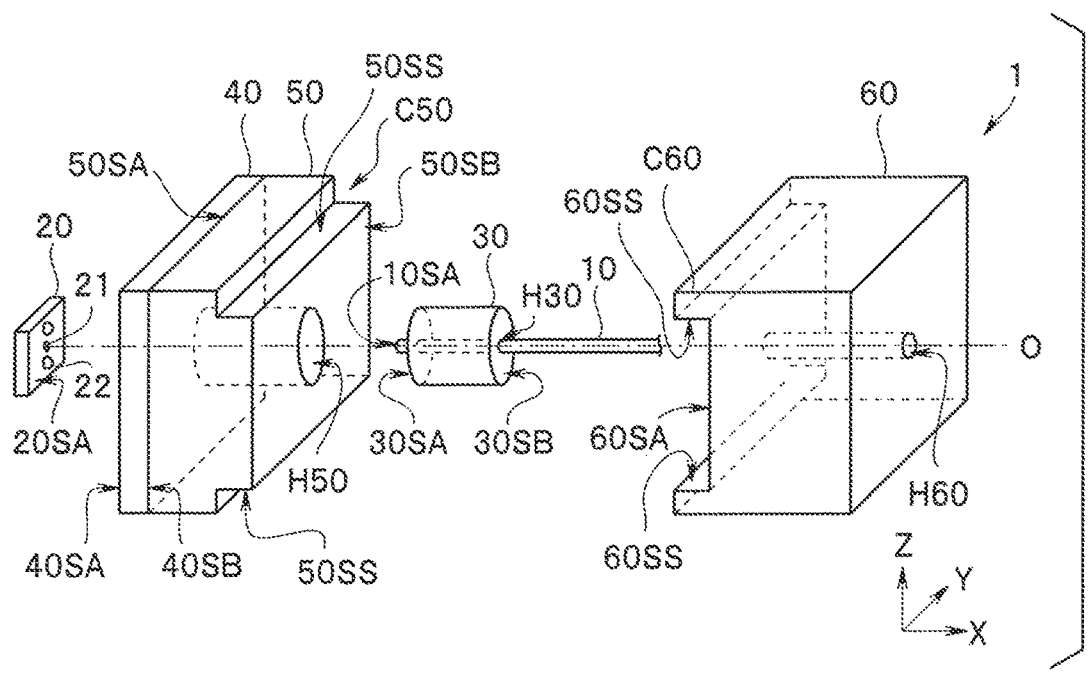
FIG. 2 is an exploded perspective view of the optical module for endoscope of the first embodiment.
Figure 3:
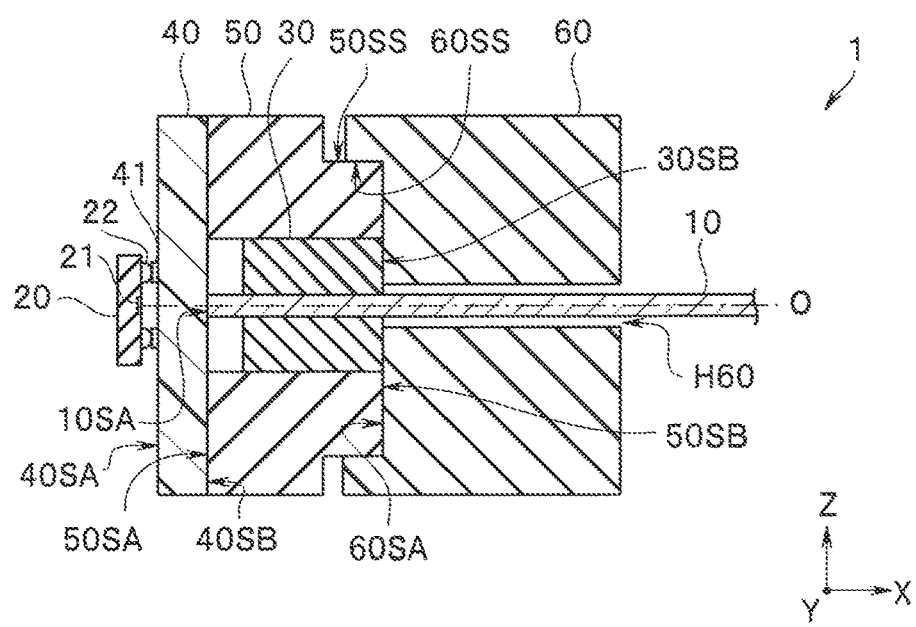
FIG. 3 is a sectional view of the optical module for endoscope of the first embodiment.

The optical module 1 illustrated in FIGS. 2 and 3 includes the optical fiber 10, a light emitting element 20 serving as an optical device, a ferrule 30, a glass substrate 40, a sleeve 50, and a stopper 60.

In the following description, the drawings according to embodiments are schematic drawings. Note that the relationship between thickness and width of individual parts, the proportion of thickness of individual parts, relative angles of individual parts, and the like are different from actual dimensions and the like. The relationship and proportion of dimensions may partially differ among the drawings. In addition, some constituent elements may be not illustrated in the drawing. It is assumed that in a direction parallel to an optical axis O the light emitting element 20 is disposed on a "front" side while the stopper 60 is provided on a "back" side.

The optical fiber 10 transmits optical signals. The optical fiber 10 includes, for example, a core of a 62.5 μm diameter for transmitting light and a cladding of an 80 μm diameter covering an outer circumferential surface of the core.

The light emitting element 20 for outputting optical signals serves as an optical device. The light emitting element 20 is a vertical-cavity surface-emitting laser (VCSEL). A light emitting section 21 is formed at a light emitting surface 20SA of the light emitting element 20. For example, when the light emitting element 20 is significantly small with plan view dimensions (outer dimensions of a cross section perpendicular to the optical axis O) of 235 μm×235 μm, the light emitting section 21 of a 10 μm diameter and an external terminal 22 of a 70 μm diameter for supplying a drive signal to the light emitting section 21 are provided at the light emitting surface 20SA of the light emitting element 20.

The ferrule 30 has a front surface 30SA and a back surface 30SB on the opposite side of the front surface 30SA. The ferrule 30 is a cylinder of a length L30 (dimension in optical axis direction) of 500 μm. The ferrule 30 has a first through-hole 1130 into which a distal end portion of the optical fiber 10 is inserted and fixed with an adhesive 35 (refer to FIG. 10). A distal end surface 10SA of the optical fiber 10 protruding from the front surface 30SA is in contact with a second principal surface 40SB of the glass substrate 40.

The glass substrate 40 has a first principal surface 40SA and the second principal surface 40SB on the opposite side of the first principal surface 40SA. The light emitting element 20 is mounted on the first principal surface 40SA. In other words, a connection electrode 41 is disposed at the first principal surface 40SA, and the connection electrode 41 is bonded to the external terminal 22 of the light emitting element 20. A drive signal is supplied to the connection electrode 41 through a wiring line, which is not illustrated in the drawings.

The sleeve 50 has a third principal surface 50SA and a fourth principal surface 50SB on the opposite side of the third principal surface 50SA. The ferrule 30 is inserted in a second through-hole H50 of the sleeve 50.

An inner diameter R50 of the second through-hole H50 of the sleeve 50 is 455 μm, while an outer diameter R30 of the ferrule 30 inserted into the second through-hole H50 is 450 μm. This means that only a slight space exists between an outer circumferential surface of the ferrule 30 and an inner surface of the second through-hole H50 of the sleeve 50. This structure is formed for the purpose of precisely matching the position of a central axis of the second through-hole H50 with the position of a central axis of the first through-hole H30 of the ferrule 30 inserted in the second through-hole H50, that is, precisely matching optical axes.

As will be described later, it is preferable that in the optical module 1 the ferrule 30 be not fixed to the sleeve 50 with an adhesive or the like.

The third principal surface 50SA of the sleeve 50 is bonded to the second principal surface 40SB of the glass substrate 40. Thus, a bottom surface of the second through-hole H50 is the second principal surface 40SB of the glass substrate 40. Note that, for example, a silicon oxide film serving as the glass substrate may be formed at the third principal surface 50SA of the sleeve 50 formed of silicon.

The stopper 60 is a pressing portion having a contact surface 60SA in surface contact with the fourth principal surface 50SB of the sleeve 50 and the back surface 30SB of the ferrule 30. The stopper 60 has a third through-hole H60 that allows insertion of the optical fiber 10. The inner diameter of the third through-hole 1160 is larger than the outer diameter of the optical fiber but smaller than the outer diameter of the ferrule 30.

The back surface 30SB of the ferrule 30 is pressed against the contact surface 60SA of the stopper 60 to remain in surface contact with the contact surface 60SA, such that the ferrule 30 is stably held in the second through-hole H50 of the sleeve 50. The contact surface 60SA of the stopper 60 has a raised portion C60. The fourth principal surface 50SB of the sleeve 50 has a depressed portion (cutout) C50. In the state in which an inner side surface 60SS of the raised portion C60 of the stopper 60 is in contact with a side surface 50SS of the depressed portion C50 of the sleeve 50, the raised portion C60 is fitted to the depressed portion C50, such that the position of a central axis of the second through-hole 1150 of the sleeve 50 and the position of a central axis of the third through-hole H60 of the stopper 60 are automatically matched with each other. Note that while in the optical module 1 two inner side surfaces 60SS of the raised portion C60 are in contact with two side surfaces 50SS of the depressed portion C50, at least one inner side surface 60SS and at least one side surface 50SS in pair need to be in contact with each other.

Since the optical module 1 has the stopper 60, the ferrule 30 does not come off when the optical fiber 10 is pulled backwards. Furthermore, since the distal end surface 10SA of the optical fiber 10 is in contact with the second principal surface 40SB of the glass substrate 40, in the optical module 1 the distance between the distal end surface 10SA and the light emitting section 21 of the light emitting element 20 always remains constant, and as a result, it is possible to maintain stable characteristics.

Note that it is possible to maintain a constant distance between the distal end surface 10SA and the light emitting section 21 of the light emitting element 20 when the distal end surface 10SA of the optical fiber 10 and the second principal surface 40SB of the glass substrate 40 are not in contact with each other but spaced apart from each other by a predetermined distance.

The optical module 1 is significantly small in size; for example, the outer dimensions of the sleeve 50 are 1 mm×1 mm. Thus, the endoscope 9 including the optical module 1 can achieve minimally invasive operation.

<Manufacturing Method of Optical Module>

Figure 4:
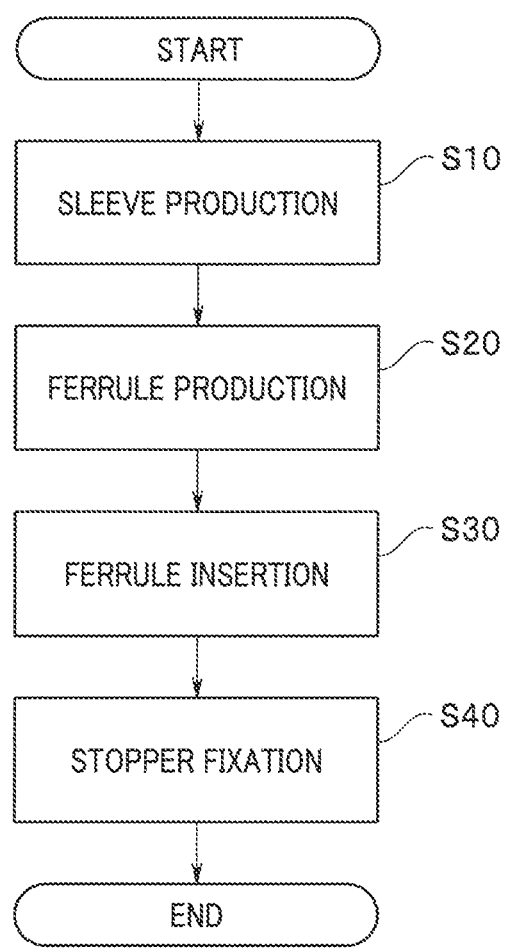
FIG. 4 is a flowchart of a manufacturing method of the optical module for endoscope of the first embodiment.

Next, a manufacturing method of the optical module 1 will be described with reference to a flowchart in FIG. 4.

<Step S10> Sleeve Production Process

The sleeve 50 is produced such that the second principal surface 40SB of the glass substrate 40 is bonded to the third principal surface 50SA.

Figure 5:
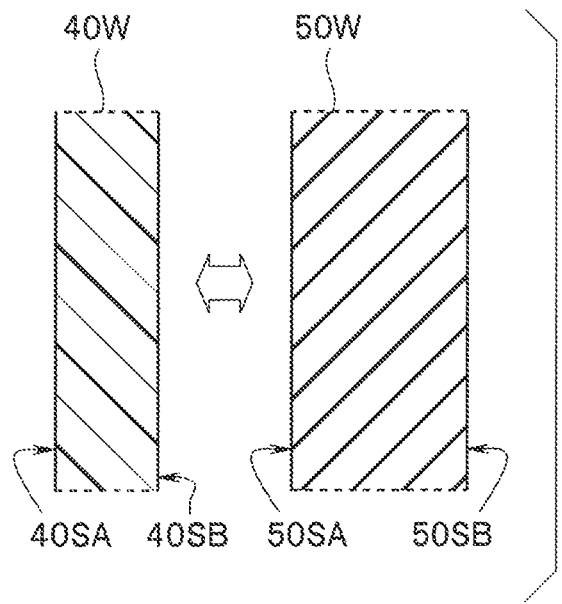
FIG. 5 is a sectional view for explaining the manufacturing method of the optical module for endoscope of the first embodiment.

In other words, as illustrated in FIG. 5, a bonded wafer is produced by, for example, anodically bonding a silicon wafer 50W and a glass wafer 40W.

An etch mask is disposed on the fourth principal surface 50SB of the silicon wafer 50W, and a dry etching process such as reactive-ion etching (RIE) is performed. While the glass wafer 40W serves as an etch stop layer, the second through-hole H50 is formed to penetrate the silicon wafer 50W. Thus, the depth of the second through-hole H50 with a bottom is a thickness D50 of the silicon wafer SOW.

The second through-hole H50 may be formed by not dry etching but wet etching. The second through-hole H50 may be formed in a cylindrical shape, or a rectangular column shape when the inner surface can hold the ferrule 30.

The glass wafer 40W is formed as a thin layer capable of sufficiently passing light of a wave length of an optical signal. It is preferable that a thickness D40 of the glass wafer 40W be 50 μm or less. The glass wafer 40W is unlikely to be damaged when the thickness D40 is 5 μm or greater.

Figure 6:
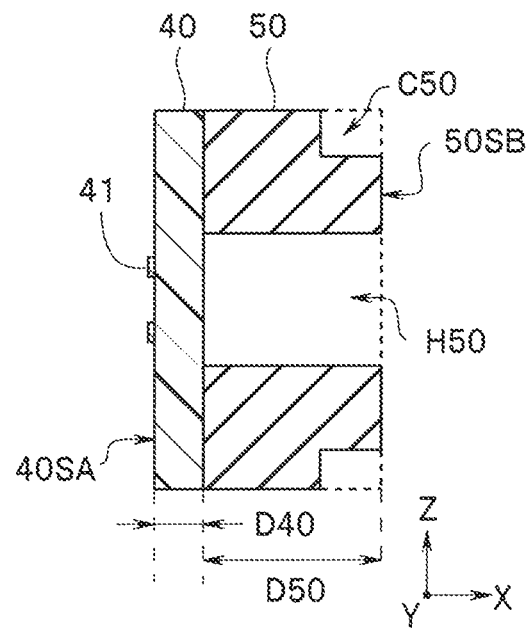
FIG. 6 is a sectional view for explaining the manufacturing method of the optical module for endoscope of the first embodiment.

The depressed portion C50 for positioning is formed at an outer circumference portion of the sleeve 50. By cutting the bonded wafer, the sleeve 50 with the glass substrate 40 illustrated in FIG. 6 is produced.

For example, the connection electrode 41 formed of gold is disposed at the first principal surface 40SA of the glass substrate 40 by performing a sputtering process.

Figure 7:
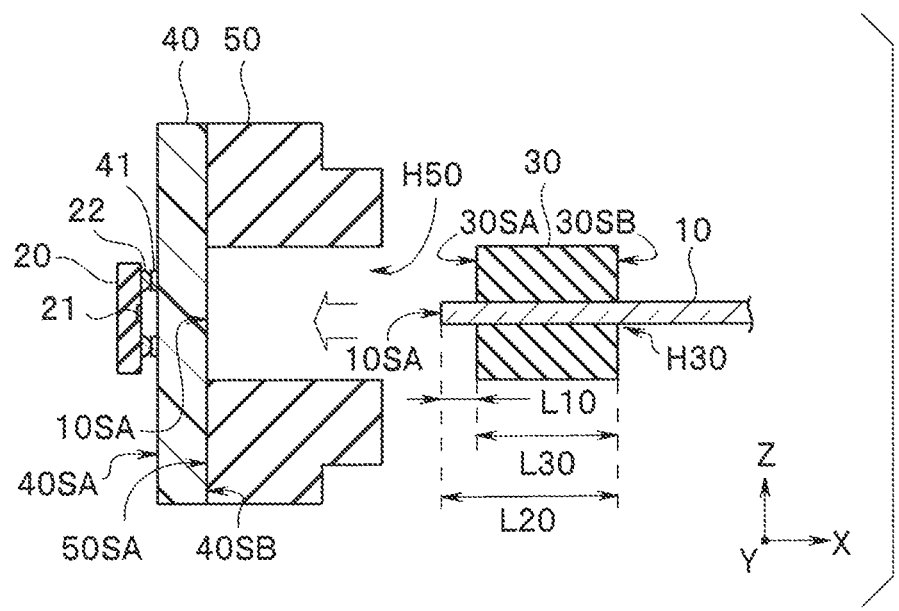
FIG. 7 is a sectional view for explaining the manufacturing method of the optical module for endoscope of the first embodiment.

As illustrated in FIG. 7, the light emitting element 20 is mounted by flip chip mounting at a position that enables the light emitting section 21 to face the second through-hole H50. In other words, the external terminal 22 of the light emitting element 20 is bonded to the connection electrode 41 of the glass substrate 40 by, for example, ultrasound bonding.

<Step S20> Ferrule Production Process

The ferrule 30 is produced such that the optical fiber 10 is inserted in the first through-hole H30.

The external shape of the ferrule 30 is a cylindrical shape but may be a quadrangle or polygonal column shape. The internal shape of the first through-hole H30 is a cylindrical shape but may be a quadrangle or polygonal column shape when the inner surface can hold the optical fiber 10. The material of the ferrule 30 is, for example, a ceramic material, a silicon material, a glass material, or a metal material such as stainless steel.

As illustrated in FIG. 7, the optical fiber 10 is positioned to allow the distal end surface 10SA to protrude from the front surface 30SA of the ferrule 30 by a length L10. The length L10 is, for example, greater than 10 μm and less than 100 μm. The optical fiber 10 is fixed to the ferrule 30 by the adhesive 35 (refer to FIG. 10). For example, the adhesive 35 formed of a thermosetting resin is subjected to a heating process at 120° C. for thirty minutes to be hardened. By using the adhesive 35 formed of an ultraviolet curable thermosetting resin, the optical fiber 10 may be fixed to the ferrule 30 by radiating ultraviolet light, and subsequently, heat hardening processing may be additionally performed.

A distance L20 between the distal end surface 10SA of the optical fiber 10 and the back surface 30SB of the ferrule 30 is the total of the length L30 of the ferrule 30 and a protrusion amount L10. For example, when the length 130 is 500 μm and the protrusion amount L10 is 50 μm, the length L20 is 550 μm.

For example, the optical fiber 10 is inserted into the ferrule 30 in the state in which the ferrule 30 is fixed to a jig for setting the protrusion length. Subsequently, in the state in which the distal end surface 10SA of the optical fiber 10 is in contact with a reference plate positioned apart by the length L10 from the front surface 30SA of the ferrule 30, the adhesive 35 is subjected to hardening processing to fix the optical fiber 10 to the ferrule 30.

<Step S30> Ferrule Insertion Process

As illustrated in FIG. 7, the ferrule 30 with the fixed optical fiber 10 is inserted into the second through-hole H50 of the sleeve 50.

As described above, to precisely match optical axes, only a slight space exists between the outer circumferential surface of the ferrule 30 and the inner circumferential surface of the second through-hole 1150 of the sleeve 50. Thus, when it is attempted to insert the ferrule 30 into the second through-hole H50 with the bottom, the air inside the second through-hole H50 does not easily flow out, and as a result, the glass substrate 40 of the small dimension of the thickness D40 may be damaged by insertion pressure.

When an adhesive is used to fix the ferrule 30 to the sleeve 50, the adhesive spreads in a narrow space. In such a particular case, the air inside the second through-hole 1150 is very unlikely to flow out, and thus, the glass substrate 40 is easily damaged. In the ferrule insertion process, it is preferable that the ferrule 30 be only inserted in the sleeve 50 but not fixed to the sleeve 50 by using an adhesive or the like.

<Step S40> Stopper Fixation Process

When a tensile stress is applied to the optical fiber 10, the ferrule 30 comes out of the sleeve 50. In particular, when the ferrule 30 is not fixed to the sleeve 50, the ferrule 30 easily comes off.

Figure 8:
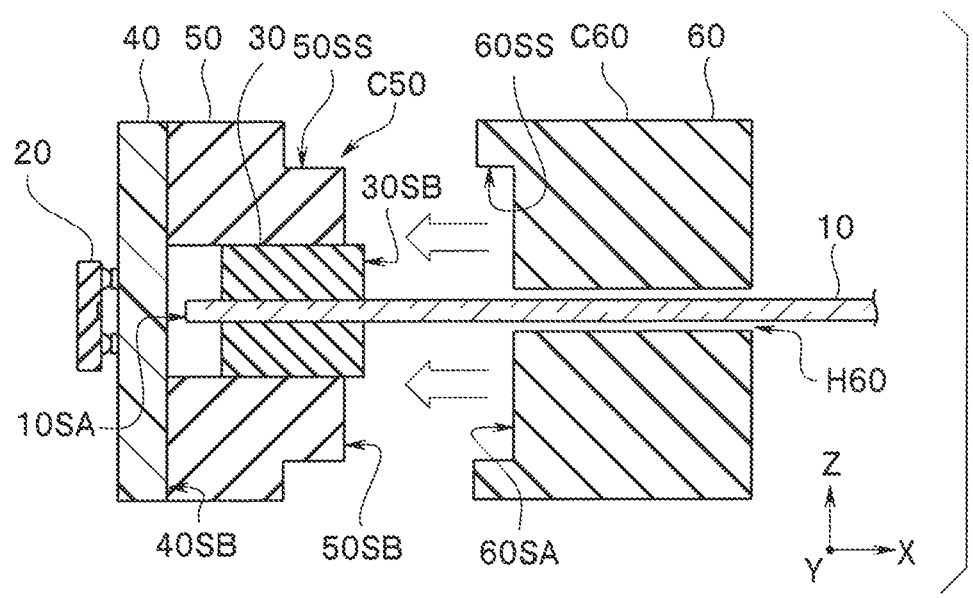
FIG. 8 is a sectional view for explaining the manufacturing method of the optical module for endoscope of the first embodiment.

In the optical module 1, as illustrated in FIG. 8, while the inner side surface 60SS of the raised portion C60 of the stopper 60 is maintained in contact with the side surface SOSS of the depressed portion C50 of the sleeve 50, the contact surface 60SA of the stopper 60 is pressed against the back surface 30SB of the ferrule 30. Accordingly, the ferrule 30 is housed in the second through-hole H50 of the sleeve 50. In the state in which the contact surface 60SA of the stopper 60 is in contact with the fourth principal surface 50SB of the sleeve 50 and the back surface 30SB of the ferrule 30, the stopper 60 is fixed to the sleeve 50 by using, for example, an adhesive. The stopper 60 may also be fixed to the ferrule 30 by using an adhesive.

The adhesive used to fix the stopper 60 may partially spread in the space between the ferrule 30 and the second through-hole H50 of the sleeve 50.

In the optical module 1, when the optical fiber 10 is pulled backwards, the ferrule 30 does not come off because the stopper 60 defines the position of the back surface 30SB of the ferrule 30. Furthermore, the optical module 1 can be relatively easily manufactured because the glass substrate 40 is unlikely to be damaged when it is attempted to insert the ferrule 30 into the sleeve 50.

The depth of the second through-hole H50, that is, the thickness (length) D50 of the sleeve 50 is identical to the length L20 between the distal end surface 10SA of the optical fiber 10 and the back surface 30SB of the ferrule 30. Thus, when the back surface 30SB of the ferrule 30 and the fourth principal surface 50SB of the sleeve 50 are disposed on the same plane, the distal end surface 10SA of the optical fiber 10 automatically comes into contact with the second principal surface 40SB of the glass substrate 40.

Since in the optical module 1 the distance between the distal end surface 10SA and the light emitting section 21 of the light emitting element 20 always remains constant, the optical module 1 can achieve stable characteristics.

Note that the protrusion length L10 from the front surface 30SA of the ferrule 30 to the distal end surface 10SA of the optical fiber 10 may increase or decrease from a set value due to unavoidable manufacturing error. In the case in which the length L10 is longer than the set value, when the stopper 60 is pushed inside until the contact surface 60SA of the stopper 60 comes into contact with the fourth principal surface 50SB of the sleeve 50, the distal end surface 10SA is strongly pressed against the second principal surface 40SB. Consequently, the distal end surface 10SA or the second principal surface 40SB may be damaged or broken, which may decrease the transmission efficiency.

Figure 9:
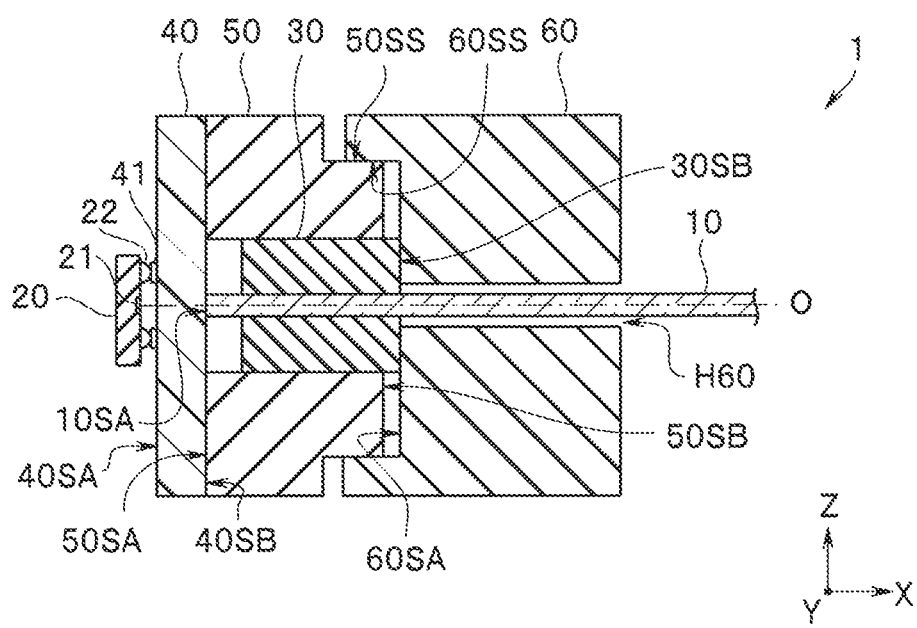
FIG. 9 is a sectional view for explaining the manufacturing method of the optical module for endoscope of the first embodiment.

Hence, it is preferable to end the operation of pushing the stopper 60 upon contact of the distal end surface 10SA with the second principal surface 40SB as illustrated in FIG. 9. The stopper 60 may be fixed to the sleeve 50 by using an adhesive in the state in which a slight space exists between the contact surface 60SA of the stopper 60 and the fourth principal surface 50SB of the sleeve 50. For example, the length of the space between the contact surface 60SA and the fourth principal surface 50SB may be 10% or less of the protrusion length L10, for example, 5 μm or less.

Alternatively, in attempting to fix the stopper 60 to the sleeve 50 while the distal end surface 10SA is in contact with the second principal surface 40SB, a slight space may be created between the distal end surface 10SA and the second principal surface 40SB before adhesive hardening processing is completed. For example, if the space between the distal end surface 10SA and the second principal surface 40SB actually exists, when the length of the space is 5 μm or less, the transmission efficiency is not significantly decreased.

This means that in the present invention "contact" does not denote complete surface contact but includes the state in which two surfaces face each other while an unavoidable but acceptable space for industrial purposes is sandwiched between the two surfaces.

Figure 10:
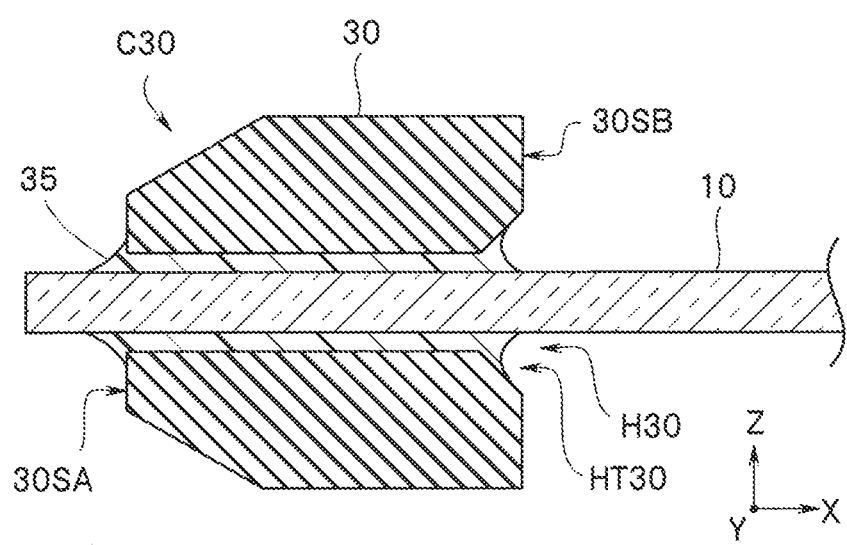
FIG. 10 is a sectional view of a ferrule of the optical module for endoscope of the embodiment.

As illustrated in FIG. 10, it is preferable that a cutout C30 be provided at an outer circumference portion of the front surface 30SA of the ferrule 30. The ferrule 30 with the cutout C30 can be easily inserted into the second through-hole H50.

As illustrated in FIG. 10, it is preferable that a taper portion HT30 be provided at an opening of the back surface 30SB of the first through-hole H30 of the ferrule 30. When it is attempted to fix the optical fiber 10 by using the adhesive 35, if an excessive unhardened portion of the adhesive 35 flows out to the back surface 30SB, the adhesive 35 spreads between the contact surface 60SA of the stopper 60 and the back surface 30SB. However, when the taper portion HT30 is provided, the excessive portion of the adhesive 35 can be stored in the taper portion HT30 as a depressed portion of the back surface 30SB, and as a result, the contact surface 60SA can be brought into contact with the back surface 30SB.

Second Embodiment

An optical module 1A of a second embodiment is similar to the optical module 1 and achieves the same effects as the effects of the optical module 1. Particular constituent elements having the same functions as functions of the optical module 1 are assigned identical reference characters, and descriptions of the particular constituent elements are not repeated.

Figure 11:
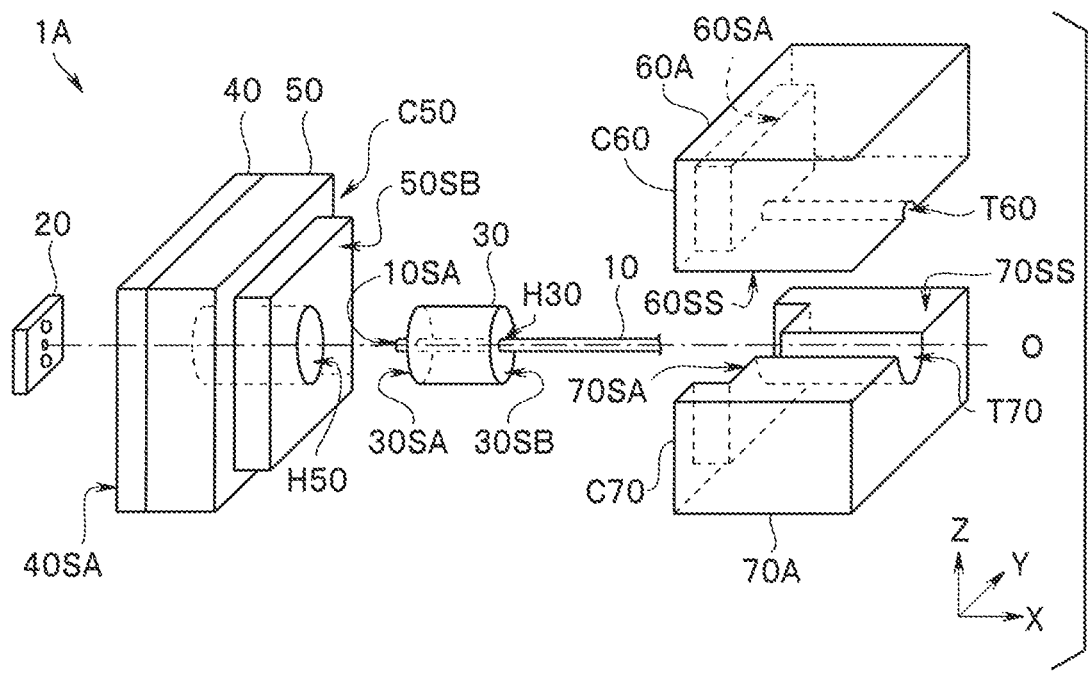
FIG. 11 is an exploded perspective view of an optical module for endoscope of a second embodiment.
Figure 12:
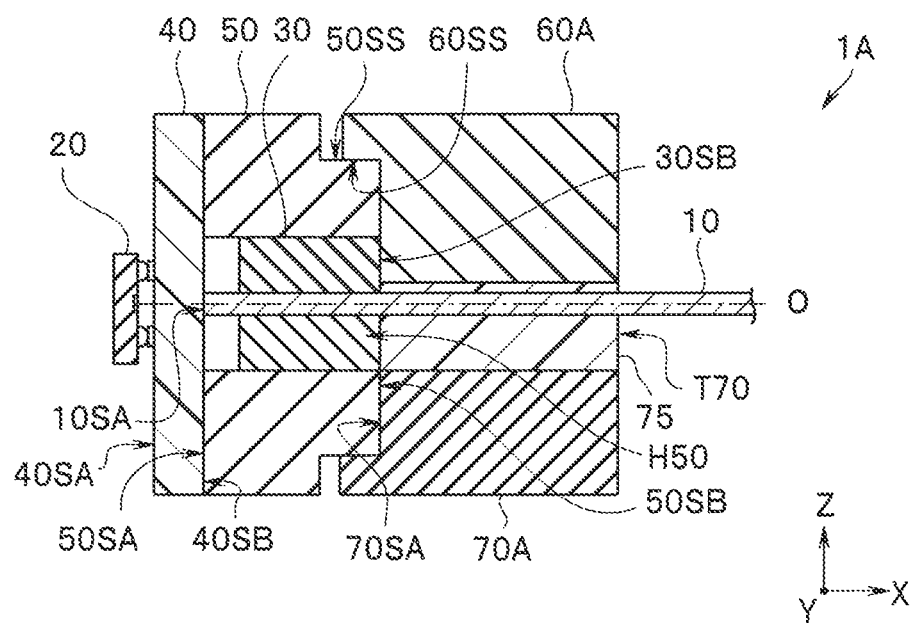
FIG. 12 is a sectional view of the optical module for endoscope of the second embodiment.

The optical module 1A illustrated in FIGS. 11 and 12 further includes a guide 70 including an upper surface 70SS having a guide groove T70 that allows insertion of the ferrule 30. A stopper 60A includes a lower surface 60SS perpendicular to the contact surface 60SA. The upper surface 70SS of the guide 70 faces the lower surface 60SS of the stopper 60A.

For example, a cross section of the guide groove T70 is a semicircle of an inner diameter slightly larger than the outer diameter of the ferrule 30. The guide groove T70 of the guide 70A and the second through-hole H50 of the sleeve 50 together form a continuous space; in other words, the lower half of the second through-hole H50 is the same in shape and size as the guide groove T70.

A groove T60 for disposing the optical fiber 10 is provided at the lower surface 60SS of the stopper 60A. For example, a cross section of the groove T60 is shaped in a semicircle of an inner diameter larger than the outer diameter of the optical fiber 10.

The stopper 60A is fixed to the sleeve 50 and the guide 70A in the state in which the contact surface 60SA abuts the fourth principal surface 50SB of the sleeve 50 and an upper portion of the back surface 30SB of the ferrule 30 in a surface contact manner. The groove T60 and the guide groove T70 are filled with a resin 75. The resin 75 holds the optical fiber 10. The inner side surface 60SS of the stopper 60A is in contact with the side surface SSS of the depressed portion C50 of the sleeve 50.

The adhesive used to bond the stopper 60A and the sleeve 50 and/or the adhesive used to bond the stopper 60A and the guide 70A may be the same thermosetting resin or the like as the thermosetting resin or the like forming the resin 75. The stopper 60A can be fixed to at least either the sleeve 50 or the guide 70A.

In a manufacturing method of the optical module 1A, a front surface 70SA perpendicular to the upper surface 70SS of the guide 70A is bonded to the fourth principal surface 50SB of the sleeve 50 by using an adhesive or anodic bonding. The depressed portion C50 of the sleeve 50 and a raised portion C70 of the guide 70A are used to match the position of the sleeve 50 and the position of the guide 70A. This means that although the depressed portion C50 and the raised portion C70 are not essential constituent elements, fitting the raised portion C70 into the depressed portion C50 can easily determine the position of the sleeve 50 and the position of the guide 70A in directions (X direction and Y direction) defined in a plane perpendicular to the optical axis O.

Figure 13:
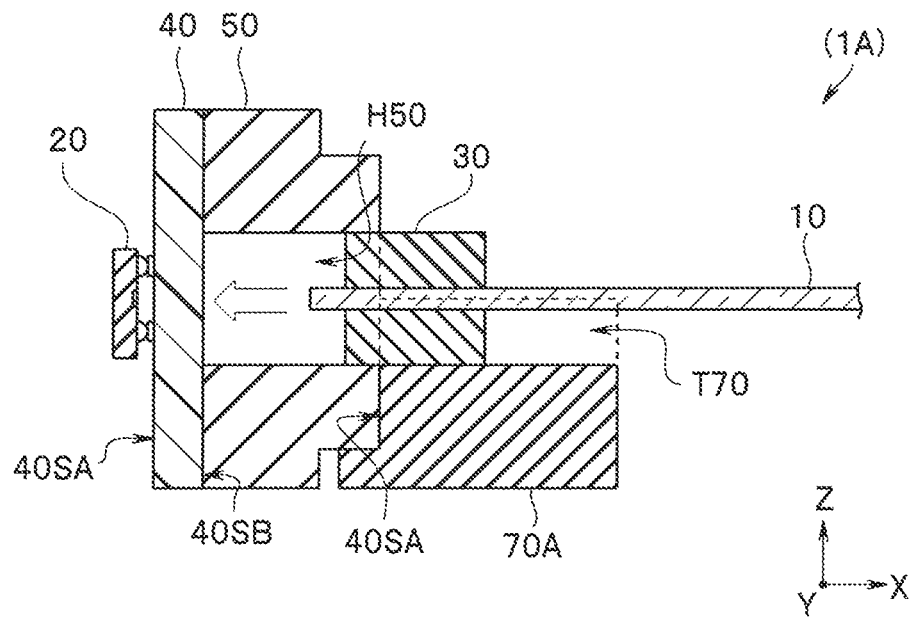
FIG. 13 is a sectional view for explaining a manufacturing method of the optical module for endoscope of the second embodiment.

As illustrated in FIG. 13, for the manufacturing method of the optical module 1A of the present embodiment, in the process of inserting the ferrule 30 (S30), a front portion of the ferrule 30 is forced into the second through-hole 1150 in the state in which a back portion of the ferrule 30 is inserted in the guide groove T70.

It is not easy to insert the small ferrule 30 into the small second through-hole H50. In addition, when aback portion of the optical fiber 10 is held in the state in which the ferrule 30 is fixed to a front portion of the optical fiber 10, the front portion of the optical fiber 10 falls down due to the weight of the ferrule 30. To insert the ferrule 30 into the second through-hole H50, it is necessary to maintain the longitudinal direction of the ferrule 30 to be parallel to the optical axis O.

By contrast, it is relatively easy to dispose a part of the ferrule 30 in the guide groove T70 having an opening at the top. After a portion of the ferrule 30 is disposed in the guide groove T70, the optical fiber 10 is pushed out, such that it is possible to relatively easily insert the ferrule 30 in the second through-hole H50.

Since the optical module 1A includes the guide 70 having the guide groove T70 with an opening at the top, it is easy to insert the ferrule 30 into the second through-hole H50.

In the optical module 1A illustrated in FIG. 12, the lower surface 60SS of the stopper 60A is in contact with the upper surface 70SS of the guide 70. However, a space may exist between the lower surface 60SS and the upper surface 70SS, and the space may be filled with a resin. In the case in which the space prevents the lower surface 60SS of the stopper 60A from being in contact with the optical fiber 10, it is unnecessary to provide a groove for disposing the optical fiber 10 in the lower surface 60SS.

In the manufacturing process of the optical module 1A, the contact surface 60SA of the stopper 60A is caused to move in a direction toward the back surface 30SB of the ferrule 30, that is, a direction of the optical axis O, to come into contact with the back surface 30SB. The contact surface 60SA may come into contact with the back surface 30SB by causing the lower surface 60SS of the stopper 60A to move in a direction toward the upper surface 70SS of the guide 70, that is, a direction perpendicular to the optical axis O.

Figure 14:
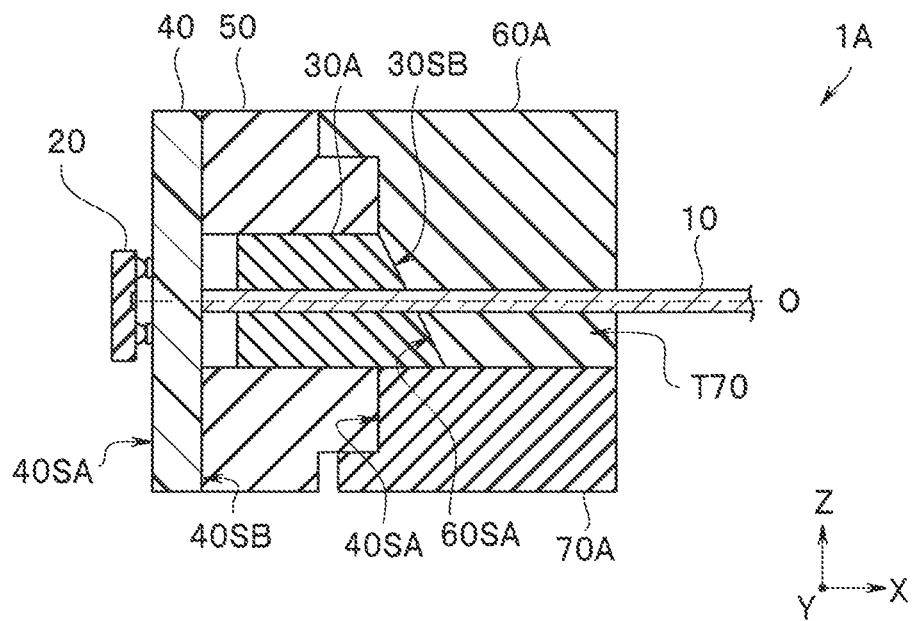
FIG. 14 is a sectional view for explaining the manufacturing method of the optical module for endoscope of the second embodiment.
Figure 15:
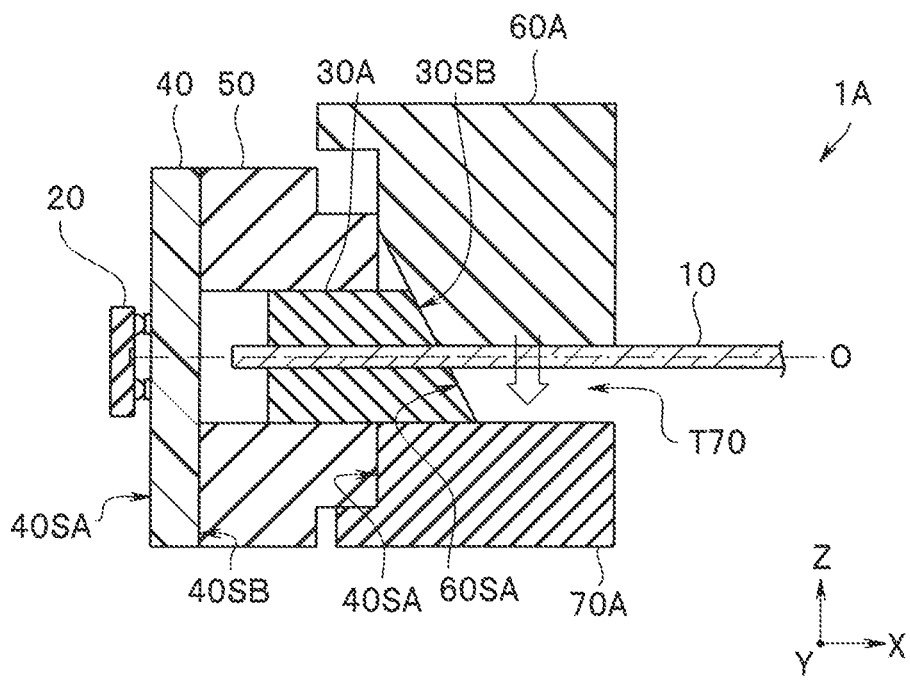
FIG. 15 is a sectional view of the optical module for endoscope of the second embodiment.

More specifically, as illustrated in FIGS. 14 and 15, the back surface 30SB of a ferrule 31 is formed as a sloping surface inclined with respect to the optical axis O. The contact surface 60SA inclined at the same angle as the inclination angle of the back surface 30SB. The contact surface 60SA can be caused to move in a direction of the guide 70A. A support member including a sloping surface may be provided at the back surface 30SB of the ferrule 31. In this case, the sloping surface of the support member can be regarded as the back surface of the ferrule.

<Modifications of Second Embodiment>

Optical modules 1B to 1E of modifications of the second embodiment are similar to the optical modules 1 and 1A and achieve the same effects as the effects of the optical modules 1 and 1A. Particular constituent elements having the same functions as functions of the optical modules 1 and 1A are assigned identical reference characters, and descriptions of the particular constituent elements are not repeated.

<First Modification of Second Embodiment>

Figure 16:
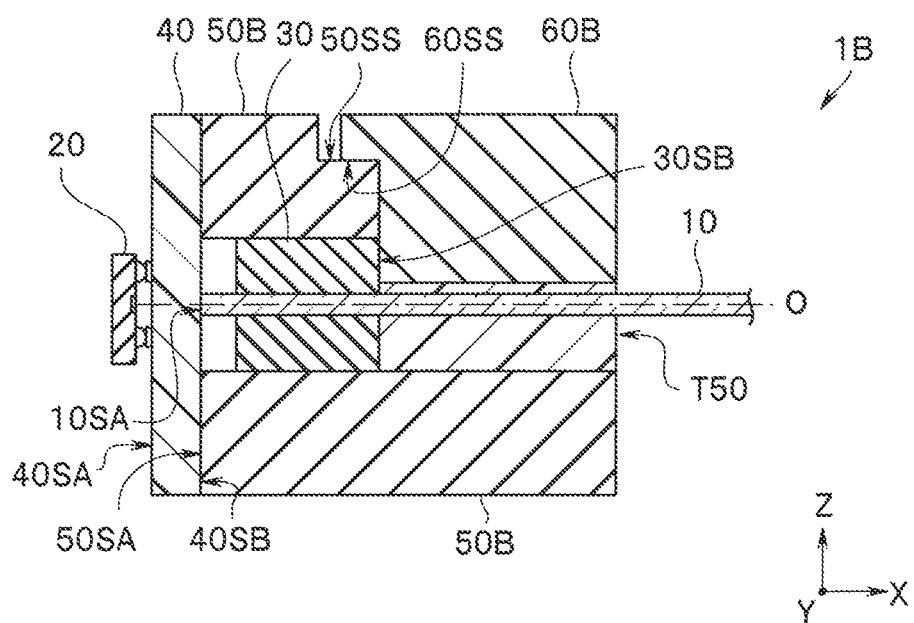
FIG. 16 is a sectional view of an optical module for endoscope of a first modification of the second embodiment.

The optical module 1B of the present modification illustrated in FIG. 16 includes a sleeve 50B having a guide groove T50, in which the sleeve and the guide are integrated together. The inner side surface 60SS of a stopper 60B is in contact with the side surface 50SS of the sleeve 50B.

Since it is unnecessary to fix the sleeve to the guide by bonding or using an adhesive to form the optical module 1B, it is relatively easy to manufacture the optical module 1B.

<Second Modification of Second Embodiment>

Figure 17:
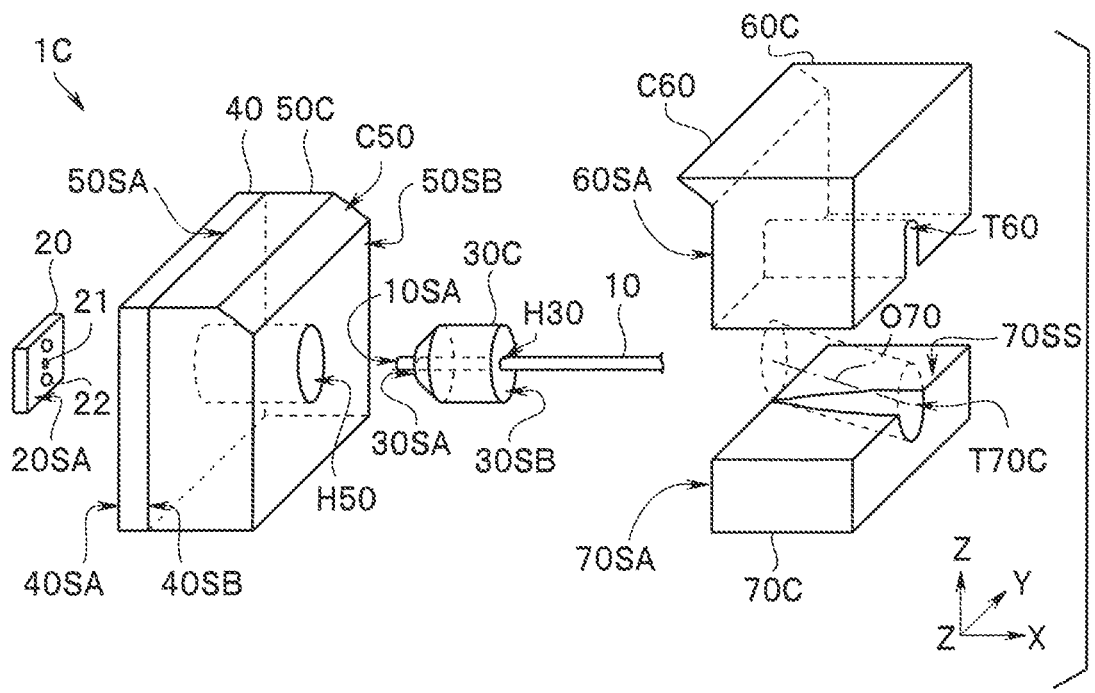
FIG. 17 is an exploded perspective view of an optical module for endoscope of a second modification of the second embodiment.
Figure 18:
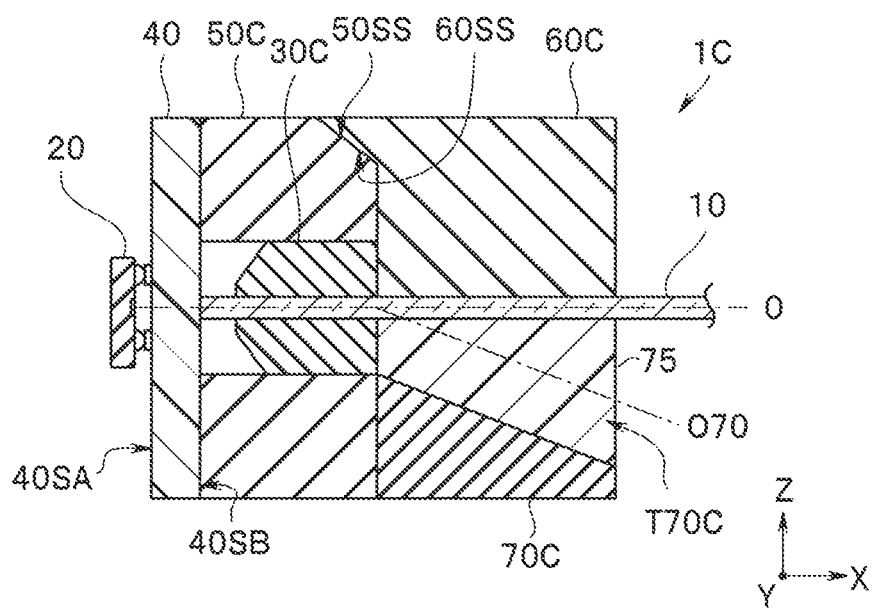
FIG. 18 is a sectional view of the optical module for endoscope of the second modification of the second embodiment.

In the optical module 1C of the present modification illustrated in FIG. 17 and FIG. 18, a guide groove T70C of a guide 70C slopes with respect to the second through-hole H50. The inner side surface 60SS of a stopper 60C is in contact with the side surface SOSS of a sleeve 50C.

This means that a central axis O70 of the guide groove T70 is in the same plane as the plane of the optical axis O as a central axis of the second through-hole H50, but the central axis O70 is not parallel to the optical axis O. The central axis O70 intersects the optical axis O at the front surface 70SA, but the distance between the central axis O70 and the optical axis O gradually increases towards the back.

Figure 19:
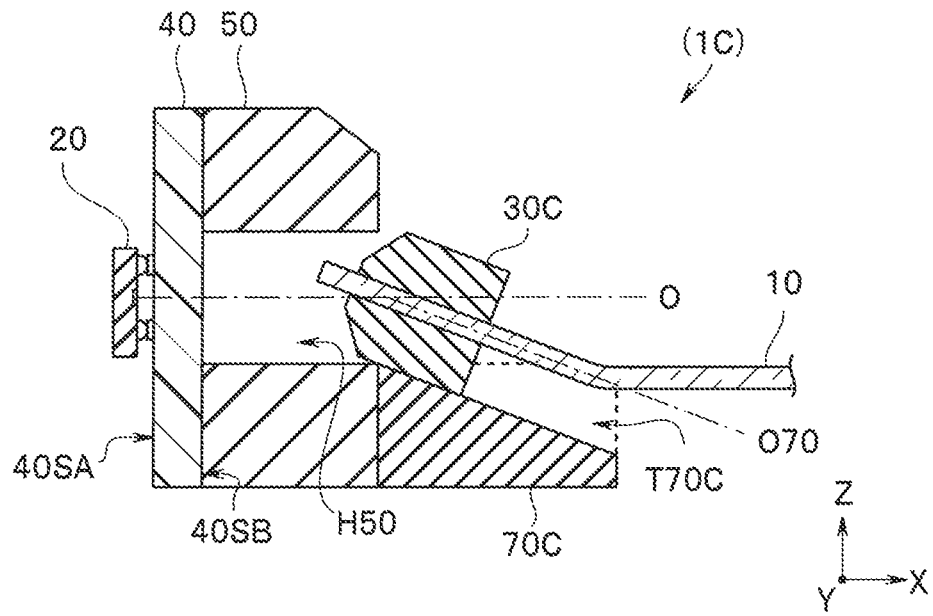
FIG. 19 is a sectional view for explaining a manufacturing method of the optical module for endoscope of the second modification of the second embodiment.

In the optical module 1C illustrated in FIG. 19, in the state in which a ferrule 30C is partially inserted in the guide groove T70, a front portion of the ferrule 30C is forced into the second through-hole H50 in a tilted state. Afterwards, the ferrule 30C gradually moves into the second through-hole H50.

It is easier to insert the ferrule 30C in the guide groove T70C inclined with respect to the optical axis O than to insert the ferrule in a guide groove parallel to the optical axis O. For example, when only a part of the outer surface of the ferrule 30C is in contact with a wall surface of the guide groove T70C, by pushing the ferrule 30C forward with the use of the optical fiber 10, the ferrule 30C can be forced into the guide groove T70C.

In the optical module 1C, as for the depressed portion C50 and the raised portion C60 for positioning the sleeve 50C and the guide 70C, each fitting surface is inclined with respect to the optical axis O. This means that when the sleeve and the guide can be properly positioned by using the depressed portion and the raised portion, the depressed portion and the raised portion can be formed in any shape, and additionally, the sleeve may have the raised portion and the guide may have the depressed portion.

<Third Modification of Second Embodiment>

Figure 20:
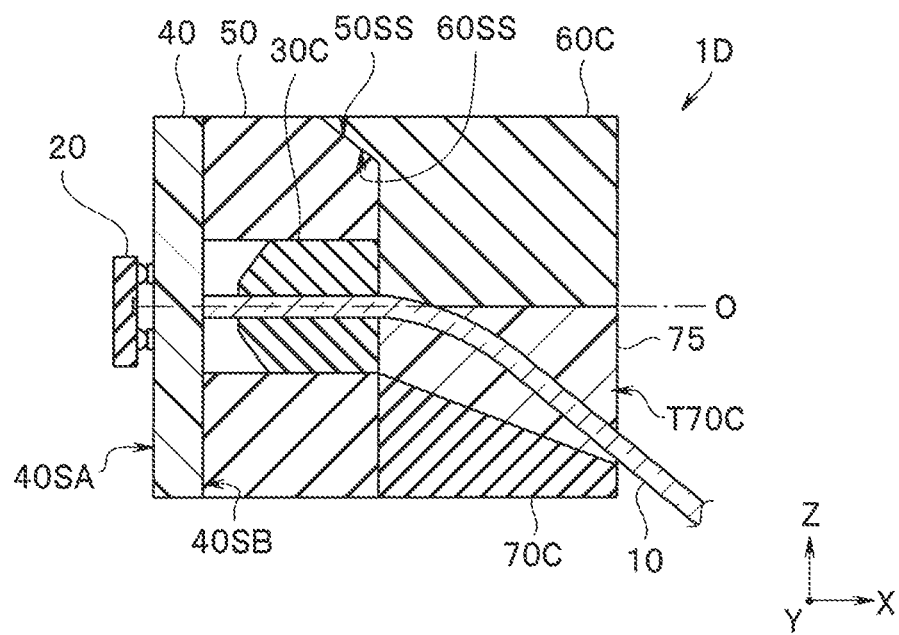
FIG. 20 is a sectional view of an optical module for endoscope of a third modification of the second embodiment.

The optical module 1D of the present modification illustrated in FIG. 20 is almost the same as the optical module 1C. As illustrated in FIG. 18, in the optical module 1C, the optical fiber 10 extends backwards along the optical axis O. By contrast, in the optical module 1D, the optical fiber 10 extends backwards along the slope of the guide groove T70C; in other words, the optical fiber 10 extends in a direction not parallel to the optical axis O.

Figure 21:
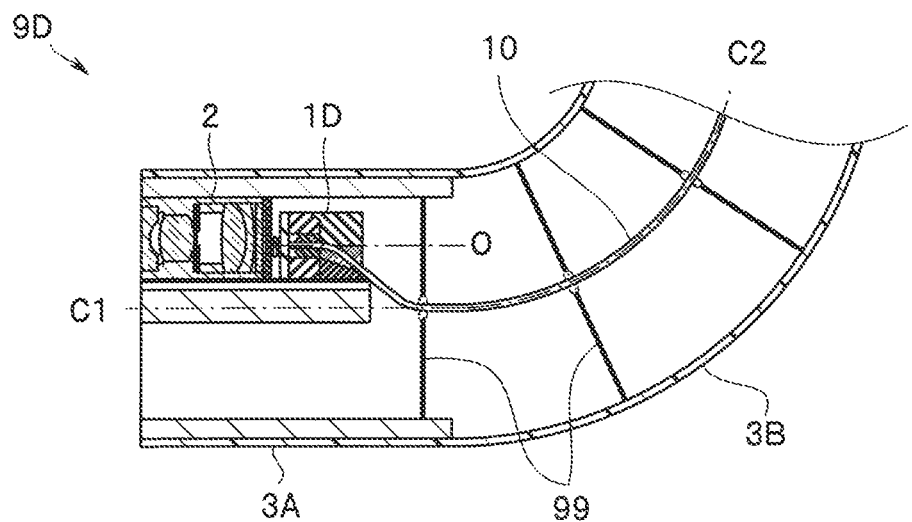
FIG. 21 is a fragmentary sectional view of an insertion section of an endoscope including the optical module for endoscope of the third modification of the second embodiment.

The optical module 1D is disposed at the distal end portion 3A of an endoscope 9D including the insertion section 3 formed by connecting the hard distal end portion 3A, the bending portion 3B, the flexible portion 3C. As illustrated in FIG. 21, the optical module 1D is disposed, together with the image pickup device 2 including an image pickup optical system, at the distal end portion 3A of the endoscope 9D.

The optical axis O of the light emitting element 20 of the optical module 1D is parallel to a distal end portion central axis C1 of the distal end portion 3A, but the optical module 1D and the distal end portion 3A do not have the same center point; in other words, the optical module 1D is not disposed on the center point of the distal end portion 3A. The optical fiber 10 extends along the slope of the guide groove T70C toward the distal end portion central axis C1; in the bending portion 3B, the optical fiber 10 is arranged along a bending portion central axis C2.

A plurality of guide members 99 are provided at a proximal end portion of the distal end portion 3A and the bending portion 3B. The guide members 99 guide the optical fiber 10 along the distal end portion central axis C1 (central axis C) and the bending portion central axis C2. For example, Japanese Patent Application Laid-Open Publication No. 2015-97589 discloses details of the guide members 99. While not illustrated in the drawings, it is preferable that the guide members 99 be provided at the flexible portion 3C. The flexible portion 3C does not deform as much as the bending portion 3B, and hence, arrangement intervals of the guide members 99 in the flexible portion 3C can be longer than arrangement intervals in the bending portion 3B.

As the guide member, a single multi-lumen tube of an outer diameter almost identical to the inner diameter of the bending portion 3B may be used in the state in which the multi-lumen tube is inserted in the bending portion 3B. In this case, the optical fiber 10 is inserted in a lumen positioned at the center of the multi-lumen tube, so that the optical fiber 10 is disposed along the bending portion central axis C2.

In the optical module 1D, the optical fiber 10 can be disposed along the bending portion central axis C2 without largely bending the optical fiber 10. Furthermore, in the optical module 1D, if the bending portion 3B largely deforms, great stress is unlikely applied to the optical fiber 10.

<Fourth Modification of Second Embodiment>

Figure 22:
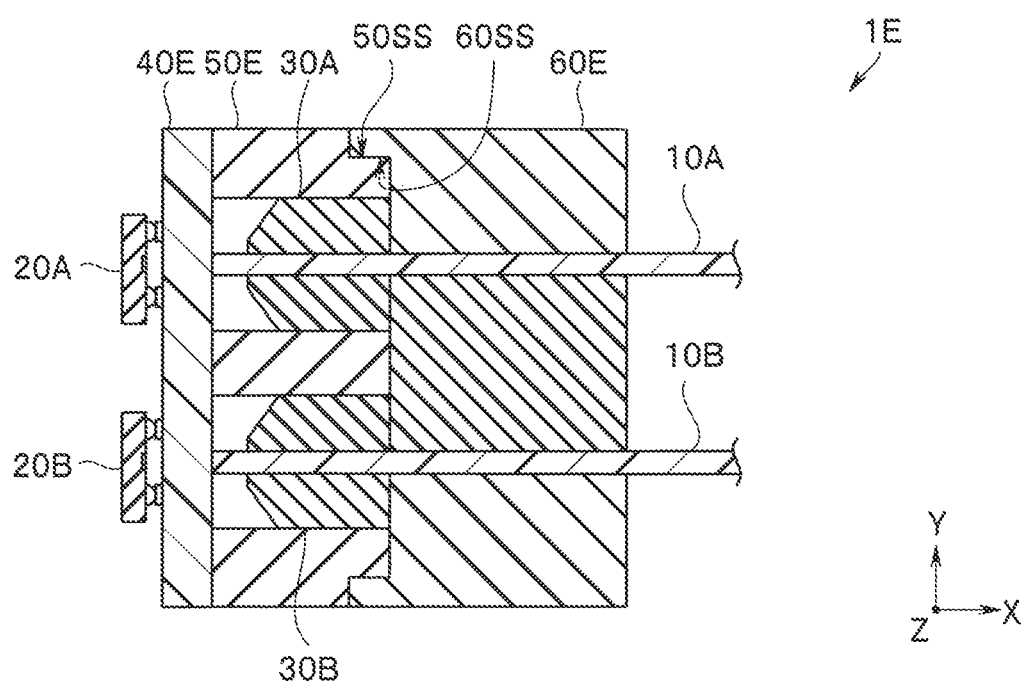
FIG. 22 is a sectional view of an optical module for endoscope of a fourth modification of the second embodiment.

In the optical module 1E of the present modification illustrated in FIG. 22, optical devices 20A and 20B are mounted in a sleeve 50E including the glass substrate 40E. A plurality of ferrules 30A and 30B (a plurality of optical fibers 10A and 10B) are inserted in the sleeve 50E and held by a single stopper 60E.

The optical module may include three or more optical devices or the like. This means that a plurality of optical devices can be disposed in a single sleeve; optical fibers can be inserted in a plurality of ferrules, and the back surface of each ferrule can be in surface contact with a contact surface of the single stopper. In other words, the optical module includes one sleeve, one stopper, at least one optical device, at least one optical fiber, and at least one ferrule.

In the optical module 1 and others, the optical device is the light emitting element 20 including the light emitting section 21. Yet, needless to say, when the optical device is an O/E optical module as a light receiving element including a light receiving unit such as a photodiode, the optical device can achieve the same effects as the effects of the optical module 1. This means that the optical device only needs to output or receive optical signals.

The optical module of the present invention may include a plurality of structures out of the structures of the optical modules 1A to 1E. Needless to say, endoscopes 9A to 9E including the optical modules 1A to 1E all achieve the effects of the endoscope 9 and the effects of the respective optical modules 1A to 1E.

The present invention is not limited to the embodiments and modifications described above. Various changes, combinations, and applications can be made without departing from the gist and scope of the invention.

What is claimed is:

1. An optical module for an endoscope comprising:
    at least one optical fiber configured to transmit an optical signal;
    at least one optical device configured to one of transmit and receive the optical signal;
    at least one ferrule including a front surface, a back surface and a first through-hole, the back surface opposing the front surface and the optical fiber being inserted into the first through-hole;
    a glass substrate including a first principal surface and a second principal surface, the second principal surface opposing the first principal surface, the optical device being mounted on the first principal surface;
    a sleeve including a third principal surface, a fourth principal surface, a second through hole and a first side surface, the fourth principal surface opposing the third principal surface, the ferrule being inserted into the second through-hole, the third principal surface being bonded to the second principal surface of the glass substrate; and
    a stopper including a contact surface in surface contact with the back surface of the ferrule, and a second side surface in contact with the first side surface of the sleeve such that the first side surface and the second side surface overlap in a radial direction of the at least one optical fiber, and the stopper being fixed to the sleeve by using an adhesive.

2. The optical module for endoscope according to claim 1, wherein a distal end surface of the optical fiber is in contact with the second principal surface of the glass substrate.

3. The optical module for endoscope according to claim 1, wherein the contact surface is in contact with the fourth principal surface.

4. The optical module for endoscope according to claim 1, further comprising:
    a guide including an upper surface having a guide groove that allows insertion of the ferrule,
    wherein the stopper includes a lower surface perpendicular to the contact surface, and
    the upper surface of the guide and the lower surface of the stopper face each other.

5. The optical module for endoscope according to claim 4, wherein the sleeve and the guide are integrated together.

6. The optical module for endoscope according to claim 4, wherein the guide groove of the guide includes a slope in relation to the second through-hole.

7. The optical module for endoscope according to claim 6, wherein the optical fiber extends backwards along the slope of the guide groove.

8. The optical module for endoscope according to claim 1, wherein the first side surface is a part of an outer surface of the sleeve and the second side surface is a mating inner surface of the stopper.

9. The optical module for endoscope according to claim 1, wherein a portion of the sleeve is arranged inside of the stopper in the radial direction.

10. The optical module for endoscope according to claim 1, wherein the first side surface of the sleeve comprises a cut-out portion, and the second side surface of the stopper comprises a raised portion, wherein the raised portion is arranged outside of the cut-out portion in the radial direction.

11. The optical module for endoscope according to claim 1, wherein the front surface of the ferrule is offset from the first principal surface of the glass substrate in a longitudinal direction of the at least one optical fiber.

12. An endoscope comprising:
    an optical module comprising:
        at least one optical fiber configured to transmit an optical signal;
        at least one optical device configured to one of transmit and receive the optical signal;
        a ferrule including a front surface, a back surface and a first through-hole, the back surface opposing the front surface and the optical fiber being inserted into the first through-hole;
        a glass substrate including a first principal surface and a second principal surface, the second principal surface opposing the first principal surface, the optical device being mounted on the first principal surface;
        a sleeve including a third principal surface, a fourth principal surface, a second through hole and a first side surface, the fourth principal surface opposing the third principal surface, the ferrule being inserted into the second through-hole, the third principal surface being bonded to the second principal surface of the glass substrate; and
        a stopper including a contact surface in surface contact with the back surface of the ferrule, and a second side surface in contact with the first side surface of the sleeve such that the first side surface and the second side surface overlap in a radial direction of the at least one optical fiber, and the stopper being fixed to the sleeve by using an adhesive.

13. The endoscope according to claim 12, wherein a distal end surface of the optical fiber is in contact with the second principal surface of the glass substrate.

14. The endoscope according to claim 12, wherein the first side surface is a part of an outer surface of the sleeve and the second side surface is a mating inner surface of the stopper.

15. The endoscope according to claim 12, wherein a portion of the sleeve is arranged inside of the stopper in the radial direction.

16. The endoscope according to claim 12, wherein the front surface of the ferrule is offset from the first principal surface of the glass substrate in a longitudinal direction of the at least one optical fiber.

17. A manufacturing method of an optical module for endoscope, the optical module for endoscope comprising:
an optical fiber configured to transmit an optical signal,
an optical device configured to one of transmit and receive the optical signal,
a ferrule including a front surface, a back surface and a first through-hole, the back surface opposing the front surface,
a glass substrate including a first principal surface and a second principal surface, the second principal surface opposing the first principal surface, the optical device being mounted on the first principal surface,
a sleeve including a third principal surface, a fourth principal surface, a second through hole and a first side surface, the fourth principal surface opposing the third principal surface, and
a stopper including a contact surface in surface contact with the back surface of the ferrule, the manufacturing method of the optical module for endoscope comprising:
producing the sleeve including the third principal surface bonded to the second principal surface of the glass substrate;
producing the ferrule including the first through-hole;
inserting the optical fiber into the first through-hole;
inserting the ferrule into the second through-hole of the sleeve; and
pressing the contact surface of the stopper against the back surface of the ferrule while the first side surface of the sleeve is maintained in contact with an inner side surface of the stopper such that the first side surface and the second side surface overlap in a radial direction of the at least one optical fiber and fixing the stopper to the sleeve in a state in which the contact surface is maintained in contact with the back surface.

18. The manufacturing method of the optical module for endoscope according to claim 17, wherein a distal end surface of the optical fiber is in contact with the second principal surface of the glass substrate.

19. The manufacturing method of the optical module for endoscope according to claim 18, wherein the contact surface is in contact with the fourth principal surface.

20. The manufacturing method of the optical module for endoscope according to claim 18, wherein
the optical module for endoscope further includes a guide including an upper surface having a guide groove that allows insertion of the ferrule, and
the inserting the ferrule includes inserting a front portion of the ferrule into the second through-hole in a state in which a back portion of the ferrule is inserted in the guide groove.

* * * * *